United States Patent [19]

Knapp et al.

[11] Patent Number: 5,345,066
[45] Date of Patent: Sep. 6, 1994

[54] DEVICE FOR HEATING SUBSTANCES UNDER THE DEVELOPMENT OF HIGH PRESSURES IN A MICROWAVE FIELD

[76] Inventors: Günter Knapp, Sorgerweg 16, A-8047 Graz; Franz Panholzer, Korosistr. 147, A-8010 Graz, both of Austria

[21] Appl. No.: 852,528

[22] Filed: Mar. 17, 1992

[30] Foreign Application Priority Data

Mar. 18, 1991 [DE] Fed. Rep. of Germany ....... 4108766

[51] Int. Cl.⁵ .............................................. H05B 6/80
[52] U.S. Cl. .................................... 219/686; 219/757; 219/759; 422/21
[58] Field of Search ................. 219/10.55 R, 10.55 E, 219/431, 440, 686, 687, 757, 759; 220/366, 367; 426/241, 243; 422/21, 22, 113

[56] References Cited

U.S. PATENT DOCUMENTS

| | | |
|---|---|---|
| 3,775,062 | 11/1973 | Susuki et al. .................... 165/155 |
| 3,831,907 | 8/1974 | Claes ................................. 259/7 |
| 4,406,861 | 9/1983 | Beauvais et al. ............. 219/10.55 R |
| 4,613,738 | 9/1986 | Saville ........................ 219/10.55 R |
| 4,877,624 | 10/1989 | Floyd et al. ................. 219/10.55 R |
| 4,882,286 | 11/1989 | Ness et al. ...................... 436/175 |
| 4,933,529 | 6/1990 | Saville ........................ 219/10.55 R |
| 4,946,797 | 8/1990 | Neas et al. ...................... 436/175 |
| 4,976,920 | 12/1990 | Jacob ................................. 422/23 |
| 5,078,924 | 1/1992 | Spinello ............................. 422/307 |
| 5,137,179 | 8/1992 | Stoffel ............................... 220/364 |

FOREIGN PATENT DOCUMENTS

| | | |
|---|---|---|
| 0145863 | 6/1985 | European Pat. Off. . |
| 0249500 | 12/1987 | European Pat. Off. . |
| 0416759 | 3/1991 | European Pat. Off. . |
| 0461383 | 12/1991 | European Pat. Off. . |
| 2753019 | 5/1979 | Fed. Rep. of Germany . |
| 3125169 | 4/1982 | Fed. Rep. of Germany . |
| 3418843 | 11/1985 | Fed. Rep. of Germany . |
| 3421778 | 1/1986 | Fed. Rep. of Germany . |
| 3606822 | 11/1987 | Fed. Rep. of Germany . |
| 3818697 | 12/1989 | Fed. Rep. of Germany . |
| 3919601 | 12/1989 | Fed. Rep. of Germany . |
| 3839049 | 5/1990 | Fed. Rep. of Germany . |
| 3928181 | 6/1990 | Fed. Rep. of Germany . |
| 4000515 | 7/1990 | Fed. Rep. of Germany . |
| 1549418 | 12/1968 | France . |
| 2452096 | 10/1980 | France . |
| 2185008 | 7/1987 | United Kingdom . |
| 2219505 | 12/1989 | United Kingdom . |
| 8001483 | 7/1980 | World Int. Prop. O. . |

OTHER PUBLICATIONS

Kingston, et al. "Introduction to Microwave Sample Preparation", American Chemical Society Reference Book, 1988, pp. 98, 101, 111.

Takashi, et al., "Plasma Processing Apparatus", Patent Abstracts of Japan, vol. 8, No. 217 (E-270), Oct. 4, 1984, JP-A-59103341.

H. M. Kingston and L. B. Jassie: Anlytical chemistry 58 (1986), pp. 2534–2541, Microwave Energy for Acid Decomposition . . . .

*Primary Examiner*—Philip H. Leung
*Attorney, Agent, or Firm*—Steinberg, Raskin & Davidson

[57] ABSTRACT

A device for heating substances under the development of high pressures in a microwave field is disclosed. Those parts of the device lying in the microwave field comprise material transparent to microwaves. The device comprises a pressure-resistant cylindrically shaped outer container and a cylindrically shaped inner container disposed inside the outer container. Both the inner and outer container is provided with a cover or a cap for closure thereof. An interspace is provided between an inner jacket surface of the outer container and an outer jacket surface of the inner container, which space is connected with a space outside the device via connecting channels. The interspace preferably contains a cooling media which is transported to and from the interspace and outer space via the connecting channels.

6 Claims, 1 Drawing Sheet

DEVICE FOR HEATING SUBSTANCES UNDER THE DEVELOPMENT OF HIGH PRESSURES IN A MICROWAVE FIELD

FIELD OF THE INVENTION

The present invention relates to a device for heating substances under the development of high pressures in a microwave field, comprising a pressure-resistant cylindrically shaped outer container with a pot-like vessel and a cap detachably connected through an outer/inner engaging connection; a cylindrically shaped inner container with a front-face opening, a cover for it, and a sealing means for the tight closing of the inner container; a pressing plunger braced elastically against the outer container acting upon the outside of the cover; wherein those parts of the device lying in the microwave field comprise a material transparent to microwaves.

BACKGROUND OF THE INVENTION

In chemical laboratory techniques, heating substances by microwaves has played an increasingly important role since the energy therein is delivered directly to the substance to be heated and does not necessarily need to be carried to it by means of heat conduction through vessel walls, as is the case with external heating. For many applications in which high temperatures and/or high pressures are to be achieved, pressure-tight vessels are used herein.

An example of such an application is the process of breaking down a substance in acid described in an overview article by H. M. Kingston and L. B. Jassie in Analytical Chemistry 58 (1986), pp. 2534–2541. This article explains the breakdown of a substance into the smallest element-specific molecules or ions with the aid of one or several acids. These can subsequently be determined qualitatively or quantitatively in an element analysis. For an acid breakdown, in general, high temperatures are required. To achieve these high temperatures, the acid is heated in a closed vessel whereby high pressures are developed.

A device for the acid breakdown of a substance in the microwave field for element analysis is described in the German Patent application (examined) 39 19 601. Use of strong acids as breakdown reagents limits the user to reaction vessels of teflon or quartz. In order to be able to close such a reaction apparatus so that it is pressure-tight, it is encased in an outer container comprising synthetic materials. The outer container is cylindrically shaped with a pot-like vessel and a cap detachably connected with one another. The reaction vessel, referred to as an inner container in the following, is also cylindrically shaped and has a front-face opening, a cover for it, and sealing means. In order to close the inner container in such a way that it is pressure tight, a pressing plunger elastically braced against the outer container presses onto the outside of the cover. Heating takes place in the microwave field of a microwave oven, wherein the entire device is exposed to the effect of the microwave field. For that reason, all parts of the device comprise a material which is transparent to microwaves.

The above-described device has the disadvantage that during heating of the substance disposed in the inner container, the synthetic outer container is heated due to heat transmission and loses its stability at high temperatures. This is also the case when an inner container comprising entirely or partially a synthetic material is used. Therefore high internal temperatures should only be used over short periods of time with long cooling periods following thereafter.

In the case of long-term heating, in contrast, the temperature in the inner container should not exceed 200°–300° C.

However, there are many materials which are difficult to break down, such as for example fats, oils, coal, coke, and synthetic materials, which require higher temperatures over longer periods of time for their breakdown. The above-described device is not optimally suited for a breakdown of these materials. The time required for a breakdown with acid in general decreases with increasing temperature; many materials whose breakdown below the above-stated temperature limit value takes a long time, could be broken down in significantly shorter time at higher temperatures.

SUMMARY OF THE INVENTION

An object of the present invention is therefore based on providing a device of the above-described type in which higher long-term temperatures can be reached.

This object and others are attained by virtue of the device of the present invention, which comprises a pressure-resistant cylindrically shaped outer container comprising a pot-like vessel, and a cap detachably connected to the outer container via an outer/inner engaging connection; a cylindrically shaped inner container having a front-face opening, a cover for the inner container, and a sealing means for closing the inner container tightly; and a pressing plunger structured and arranged to act upon an outer portion of the cover for the inner container which is elastically braced against the outer container. Those parts of the device lying in the microwave field comprise a material transparent to microwaves. The device of the present invention further includes an interspace between an inner jacket surface of the outer container and an outer jacket surface of the inner container, and connecting channels from the interspace to a space outside the outer container for carrying a cooling means to and fro.

The cooling means flows through the interspace and serves for the thermal decoupling of inner and outer container and for cooling the inner container. Advantageously, the distance from the inner jacket surface of the outer container to the outer jacket surface of the inner container is 1/50 to ½ of the outer diameter of the inner container. The inner container is held in place through at least one radial spacer disposed in the vicinity of the opening of the inner container between the inner container or the cover of the inner container and the outer container. Only a portion of the bottom surface not in contact, like the jacket surface of the inner container, has an interspace relative to the outer container and the cooling media flows around it.

The connecting channels are preferably disposed so that the cooling media flows uniformly around the inner container. Air is preferably used as the cooling media, but other gaseous or liquid substances can also be used, provided that they absorb microwaves not at all or only weakly. The cooling media can be pressed or drawn by pump-like transport means through the connecting channels and the interspace. However, gaseous cooling medias can also be taken from a pressure tank and carried through the device.

In the device according to the invention the outer container retains its stability due to the cooling even at relatively high internal temperatures. In embodiments with inner containers comprising entirely or partially synthetic materials, the cooling has also an advantageous effect on the stability of the inner container. In this manner, long-term temperatures of 400° C. and above are achieved. In the case of breaking down a substance in acid, for example, this has the advantage that many of the stated materials which are difficult to break down can be broken down and that the breakdown times of materials which can be broken down at lower temperatures are generally decreased considerably.

Heating in the microwave field, for example, can also take place in a hollow space or hollow waveguide resonator. In this case, the device can be disposed so that it is only exposed to the microwave field in the area of the pot-like vessel. The cover area with pressure sensor and everything associated with it not exposed to the microwave field can comprise customary materials which do not need to be transparent to microwaves.

BRIEF DESCRIPTION OF THE DRAWINGS

The following drawing is illustrative of an embodiment of the invention and is not meant to limit the scope of the invention as encompassed by the claims.

DETAILED DESCRIPTION

Figure 1:
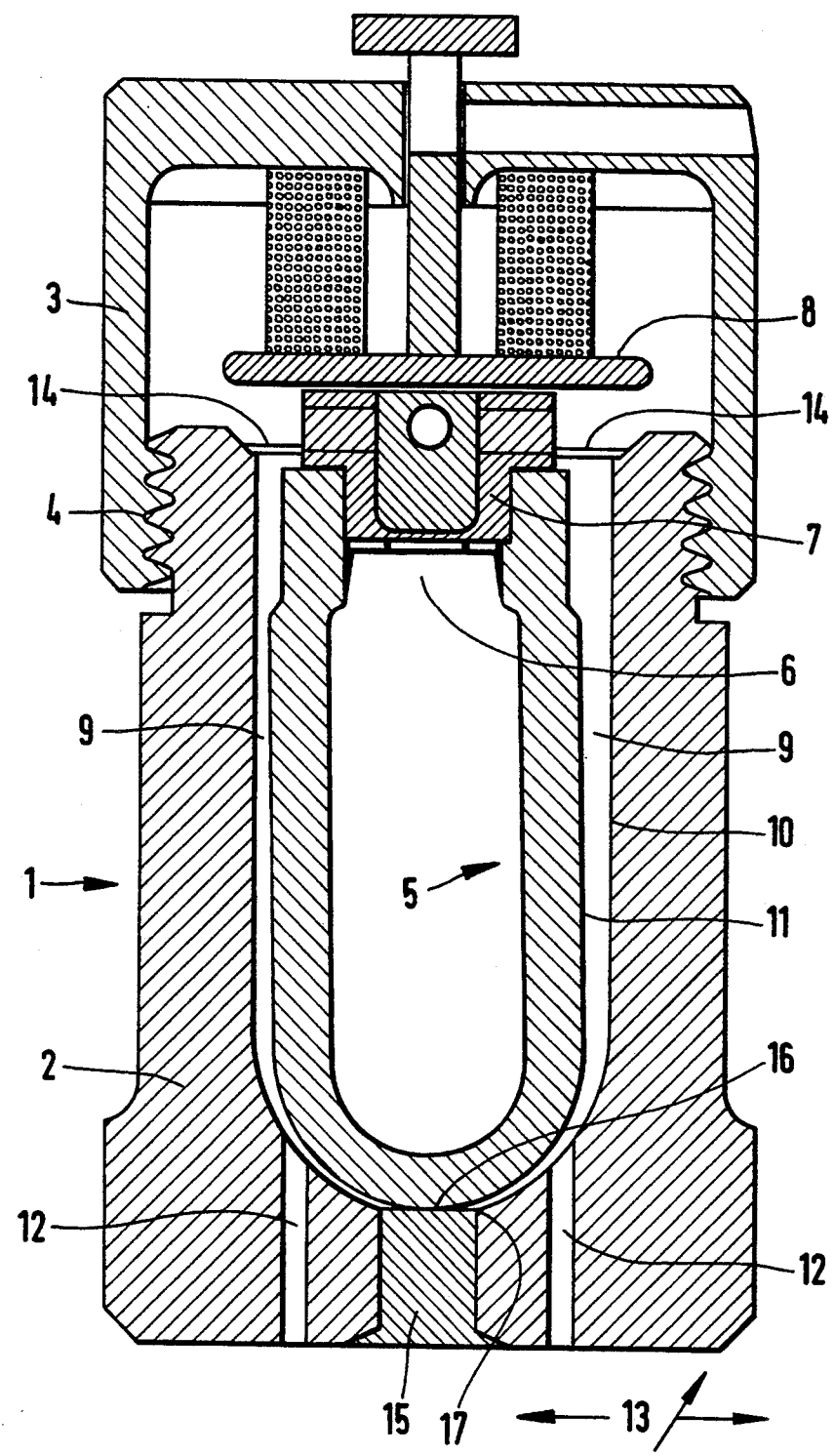
FIG. 1 depicts an axial section through a device according to the invention.

An embodiment will be described by example in further detail in conjunction with FIG. 1; the Figure depicts a section (axial section) through a device according to the invention.

The embodiment shown comprises an outer container (1) made of a synthetic material and an inner container (5) disposed therein which is made of quartz glass.

The outer container (1) comprises a pot-like vessel (2) and a cap (3) connected detachably to the outer container through an outer/inner engaging connection (4).

The inner container (5) has a front-face opening (6) and a cover (7) for the front-face opening (6). Sealing means (not shown) are preferably provided for the tight closing of the inner container (5). The sealing means can be, for example, a ring or lip seal. A pressing plunger (8) acts against the outside of the cover (7). The pressing plunger (8) is elastically braced against the cap (3) of the outer container (1).

Between the inner jacket surface (10) of the outer container (1) and the outer jacket surface (11) of the inner container (50 is disposed an interspace (9) filled with a cooling media. Connecting channels (12) connect the interspace (9) with the outer space (13) for carrying the cooling media to and fro. A radial spacer (14) in the vicinity of the opening (6) of the inner container (5) centers the inner container (5).

The outer container (1) comprises an axial bore (15) on the bottom side for pushing the inner container (5) out of the outer container (1). The bottom (16) of the inner container (5) rests on an inside edge (17) of the opening of the bore (15). The greater portion of the bottom (16) of the inner container is exposed. The inner container (5) is consequently also cooled in the area of the bottom (15).

The example provided above is not meant to be exclusive. Many other variations of the present invention would be obvious to those skilled in the art, and are contemplated to be within the scope of the appended claims.

What is claimed is:

1. A device for heating substances under the development of high pressures in a microwave field, comprising
 a pressure-resistant cylindrically shaped outer container comprising a pot-like vessel and having an opening, an outer cap detachably connected to said pot-like vessel via an outer/inner engaging connection so as to open or close said pot-like vessel,
 a cylindrically shaped inner container disposed in an inner portion of said pot-like vessel, said inner container comprising a front-face opening, a cover for said front-face opening, and sealing means for closing the inner container tightly,
 a pressing plunger structured and arranged to act upon the outside of the cover to seal said inner container, said pressing plunger being elastically braced against said outer container, wherein those parts of the device lying in the microwave field comprise a material transparent to microwaves,
 an interspace located between an inner jacket surface of said outer container and an outer jacket surface of said inner container, said interspace containing a cooling media,
 said outer container further comprising connecting channels running from an outer surface of said outer container to said interspace, said connecting channels adapted to allow said cooling media to flow between said interspace and a space outside said device.

2. The device of claim 1, wherein the distance from said inner jacket surface of said outer container to said outer jacket surface of said inner container is from about 1/50 to about ½ of the outer diameter of the inner container.

3. The device of claim 2, further comprising at least one radial spacer disposed in the vicinity of said opening of said inner container between said inner container and said outer container.

4. The device of claim 3, wherein said at least one radial spacer is disposed between said cover of said inner container and said outer container.

5. The device of claim 1, wherein said cooling media is a gas or liquid which substantially does not absorb microwaves.

6. The device of claim 1, wherein said cooling media is air.

* * * * *